United States Patent
Jämsen et al.

(10) Patent No.: US 7,328,612 B2
(45) Date of Patent: Feb. 12, 2008

(54) METHOD AND APPARATUS FOR DETECTING TYPES OF EXERCISE

(75) Inventors: Ari Jämsen, Oulu (FI); Janne Göös, Kempele (FI); Veikko Koivumaa, Espoo (FI); Eero Punkka, Helsinki (FI)

(73) Assignee: Newtest OY, Oulu (FI)

( * ) Notice: Subject to any disclaimer, the term of this patent is extended or adjusted under 35 U.S.C. 154(b) by 0 days.

(21) Appl. No.: 10/563,989

(22) PCT Filed: Jul. 8, 2004

(86) PCT No.: PCT/FI2004/000435
§ 371 (c)(1),
(2), (4) Date: Feb. 9, 2007

(87) PCT Pub. No.: WO2005/004719
PCT Pub. Date: Jan. 20, 2005

(65) Prior Publication Data
US 2007/0173377 A1    Jul. 26, 2007

(30) Foreign Application Priority Data
Jul. 9, 2003   (FI) .................................. 20031046

(51) Int. Cl.
A61B 5/22   (2006.01)
(52) U.S. Cl. .................................. 73/379.01
(58) Field of Classification Search ............. 73/379.01, 73/379, 865.4; 340/686.1
See application file for complete search history.

(56) References Cited
U.S. PATENT DOCUMENTS

| | | | |
|---|---|---|---|
| 4,144,568 A | 3/1979 | Hiller et al. | |
| 4,192,000 A | 3/1980 | Lipsey | |
| 5,447,524 A * | 9/1995 | Alt | 607/19 |
| 5,749,372 A | 5/1998 | Allen et al. | |
| 5,989,200 A | 11/1999 | Yoshimura et al. | |
| 6,145,389 A | 11/2000 | Ebeling et al. | |
| 6,349,126 B2 | 2/2002 | Ogawa et al. | |
| 6,436,052 B1 | 8/2002 | Nikolic et al. | |
| 6,700,499 B2 | 3/2004 | Kubo et al. | |
| 2006/0020177 A1 * | 1/2006 | Seo et al. | 600/300 |

FOREIGN PATENT DOCUMENTS

| | | |
|---|---|---|
| JP | 8126632 | 5/1996 |
| JP | 8131425 | 5/1996 |
| JP | 8308820 | 11/1996 |
| JP | 11347021 | 12/1999 |
| JP | 2002263086 | 9/2002 |
| JP | 2003093566 | 4/2003 |
| JP | 2003331063 | 11/2003 |

* cited by examiner

Primary Examiner—Jewel Thompson
(74) Attorney, Agent, or Firm—Volpe and Koenig P.C.

(57) ABSTRACT

The invention relates to a method and device for detecting the type of physical exercise, in which method the accelerations caused by the exercise of a person are measured by an exercise type detector (10) in three dimensions and in which characteristics describing the acceleration, so-called membership degree functions, are calculated from the measurement results, by means of which characteristics the type of exercise is detected. In the method according to the invention, only an identifier indicating the type of exercise is saved in the memory of the exercise type detector, for which reason the memory capacity required in the device is small.

27 Claims, 2 Drawing Sheets

METHOD AND APPARATUS FOR DETECTING TYPES OF EXERCISE

FIELD OF THE INVENTION

The invention relates to a method for performing the detection of the type of physical exercise, in which method the accelerations caused by a person's exercise are measured by an exercise type detector in three dimensions and in which characteristics describing the acceleration are calculated from the measurement results, by means of which characteristics the type of exercise is detected. The invention also relates to an exercise type detector utilizing the method and a program application utilized in the detector.

BACKGROUND

It is well known that the quantity and quality of physical exercise taken by a person has a significant effect on his/her present and future state of health. A well-known way to reduce the likelihood of heart disease is to stress the heart with suitable exercise/level of strain. The quantity and quality of exercise stimulating the function of the heart can be monitored by a great variety of methods and arrangements. One well known way is to measure the heart rate during the exercise/stress by a heart rate monitor, the readings of which can be examined either in real time or by means of data collected in some data collecting device in no-real time. Research information that can be utilized by the users of heart rate monitors exists about suitable levels of heart rate and the duration of the stresses.

Weight control is also one of the central factors influencing one's health on a general level. If more energy from the food eaten is stored in the tissues of a person than is consumed daily on an average, it inevitably leads to an increase of the weight. Therefore, what is needed is a kind of easy-to-use calorimeter, which measures the energy consumption of a person continuously and easily.

One solution has been presented in the patent publication U.S. Pat. No. 5,749,372. It has made known a set of equipment carried along by a person, by means of which the intensity of the exercise performed by a person can be monitored by means of acceleration measurements. The set of equipment gives the user various acoustic signals, if some predetermined level of exercise has been achieved. The target can be, for example, consuming a certain amount of energy per day. When required, the measurement results of a number of days can be saved in the device, and they can be transferred to an external device through a separate interface. The intensity of the exercise is measured by an acceleration transducer belonging to the device.

Different kinds of exercise stress different parts of the body in different ways. Therefore, by merely monitoring the heart rate it is not possible to get full information on the kind of exercise being performed. A method in which the health effects discovered from measuring the accelerations experienced by the person performing the exercise are utilized, has been presented in the patent application PCT/FI2002/001038. In this application, the effect of the accelerations caused by physical exercise on the development of the bones is described.

A measurement device for the energy consumption caused by physical exercise has been presented in the patent application U.S. Pat. No. 5,989,200. The device includes an acceleration transducer, which measures the movements of the body in one dimension. The type of exercise being performed by the person, the amount of exercise, the force used and the energy consumption of the person are calculated from the acceleration measurements. The measurement device classifies and detects the movements of the body according to a few basic types of exercise. These are sleeping, sitting, standing, walking or running. The energy consumption taking place during each type of exercise has been defined. The detection of the type of exercise is carried out either by using a characteristic describing the exercise, obtained from the acceleration measurements, or a form of acceleration signal describing the exercise. The primary way of detection is the averaging of the peak values of the acceleration maximums for a certain period of time. The decision on the type of exercise is taken on the basis of the calculated average. With the device according to the patent, the detection of the type of exercise can only be carried out on a coarse level. In addition, for detecting the type of exercise, the acceleration signal must also be averaged for a relatively long time. The measuring time must be at least 10s in order to get a result.

The detection of various types of exercise can also be utilized in short-range positioning methods. In them it is attempted to find out how and in which direction the person is moving at any given moment. When the starting point, the form of exercise and duration are known, it can be concluded where the person is at the moment. One possible algorithm has been presented in the journal "International Symposium on Wearable Computers" in its issue of October 2001. The title of the article is "Incremental Motion-Based Location Recognition" and its writers are Seon-Woo Lee and Kenji Mase. In this reference, a method is presented in which the measurement information of two acceleration transducers and a digital angle sensor and/or compass are fed to a decision-making circuit using fuzzy logic. The circuit concludes what the person is doing: Is the person immobile, walking, ascending stairs or descending stairs. It is possible to perform the arrangement presented by an arrangement which in addition to the sensor unit includes one PDA device (Personal Digital Assistant). The PDA device must have a memory of at least 32 Mbit so that the method could be utilized. In addition, the number of different types to be detected is very limited.

SUMMARY

It is an objective of the invention to present a method and a device utilizing the method, by means of which the type of the exercise performed by a person can be detected continuously during the exercise. The detection made is preferably saved in the measurement device for a post-analysis made of the exercise.

The objectives of the invention are achieved by a procedure in which the acceleration information created during the exercise of a person is measured in one, two or three dimensions/extents. This acceleration measurement information is compared to the information of a comparison table saved in the measurement device, describing different types of exercise. Only this obtained comparison result is saved in the memory of the device, and thus the memory capacity required in the measurement device is substantially reduced.

The invention has the advantage that many different types of exercise can be reliably detected by it.

In addition, the invention has the advantage that by the measurement device it is also possible to detect subtypes of the same type of exercise, such as slow walking, normal walking and fast walking.

In addition, the invention has the advantage that the measurement device uses less memory capacity than prior art devices.

The method, measurement device and computer program product according to the invention are characterized in what is set forth in the independent claims.

Some preferred embodiments of the invention have been presented in the dependent claims.

The basic idea of the invention is the following: A person carries along an exercise type detection device according to the invention. The device comprises acceleration measurement transducers preferably in three dimensions perpendicular to each other (x, y and z). One measurement period of the exercise type detection device is preferably 4 seconds. During the measurement period, all the peak values of acceleration are measured in said three dimensions. After the measurement period, 1 second is used for calculating the results and determining the calculation result as compared to a comparison table saved in the device. The value of the comparison table obtained tells which type of exercise the person was performing during the measurement period. Only this type of exercise obtained by means of comparison is saved in the memory of the device, which saves the memory capacity required in the device considerably. When the analyzing stage is over, a new measurement period of 4 seconds follows, which is again followed by a new analyzing stage. In this way, the exercise information of several days is saved continuously in periods of 5 seconds in the memory of the device, and it can be utilized in different kinds of analysis.

BRIEF DESCRIPTION OF THE DRAWINGS

In the following, the invention will be described in more detail. Reference will be made to the accompanying figures, in which.

Figure 1:
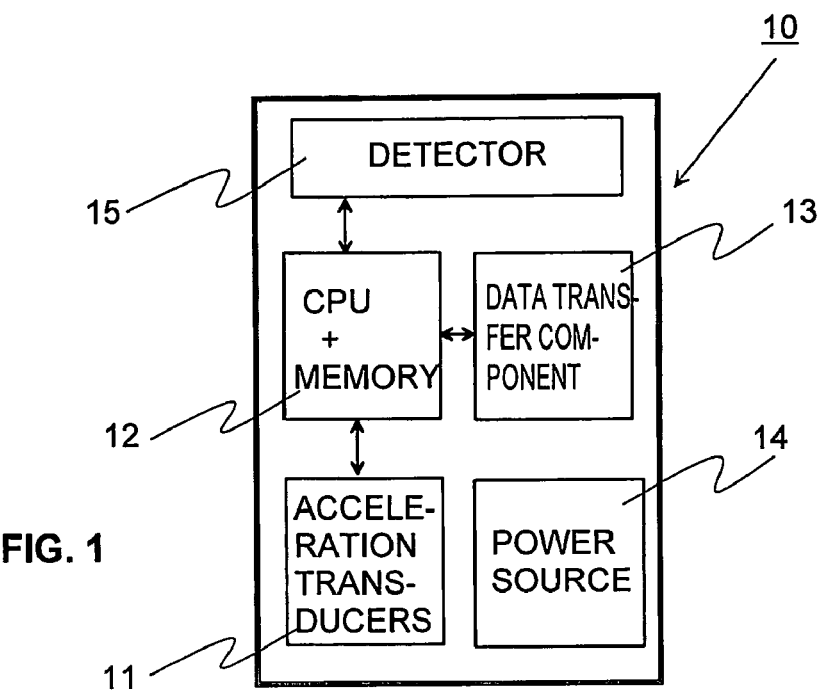
FIG. 1 shows an example of the main parts of an exercise type detection measurement device according to the invention.

In a preferred embodiment according to FIG. 1, the exercise type detector 10 measures the forces directed to the supportive organs of a person by continuously measuring the accelerations directed to the lower limbs of a person. The exercise type detector 10 measures the accelerations directed to a person by acceleration transducers 11 preferably in three different dimensions (x, y and z). The central and memory unit 12 processes this measurement information in a manner to be described later. The exercise type detector 10 preferably also includes a detector unit 15 and a data transfer component 13. By means of the data transfer component 13, the information collected by the exercise type detector 10 can be transferred to some external data processing device. The energy required by the exercise type detector 10 is obtained from a power source 14, which is preferably a chargeable accumulator.

In a preferred embodiment of the invention, the exercise type detector also comprises an altimeter based on atmospheric pressure (not presented in FIG. 1). By means of the altimeter, the movement of the person can also be monitored in the upward or downward direction. The result obtained from the altimeter is a relative change of height, from which the distance traveled by the person upwards or downwards, for example, can be calculated. This information can be advantageously utilized in connection with the exercise type detector when estimating the energy consumption of the person. Because a relative change of height is sufficient in this application, the absolute reading of the altimeter need not be calibrated for the measurement.

In another preferred embodiment of the invention, the altimeter is located in some other device carried along by the person. Such a device could be, for example, the wrist computer t6 of Suunto Oy. In this embodiment, the measurement results of the altimeter are advantageously transmitted through a wireless data transfer connection to an exercise type detector 10. The detector can use the relative height information in addition to the measured acceleration information in connection with the detection of certain types of exercise.

Figure 2:
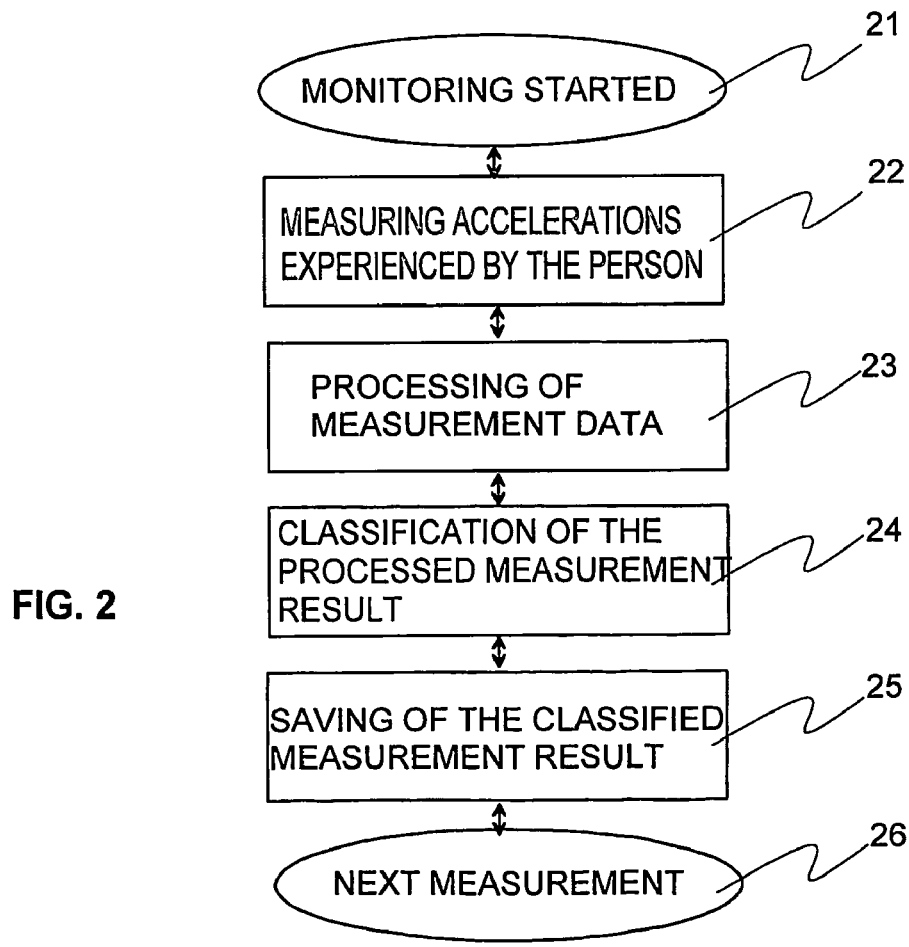
FIG. 2 shows an exemplary flow chart of the main steps of an exercise type detection method according to the invention.

FIG. 2 shows an exemplary flow chart of the main steps of the method used by the exercise type detector 10 according to the invention. The method steps described in the following can be advantageously implemented by a software application, which has been saved in the memory 12 of the exercise type detector 10.

In step 21, monitoring of the exercise is started. In step 22, accelerations are measured in three different dimensions. One measurement period is preferably 4 seconds. In step 23, the measured acceleration information is processed in a manner described hereinafter. In step 24, the processed measurement results are compared to the comparison information saved in the memory of the exercise type detector 10. This comparison information preferably comprises a plurality of various characteristics saved experimentally and describing a certain type of exercise. As a result of the comparison, the results of the measurement period are classified as belonging to a certain exercise class. In step 25, this classification result is saved in the memory of the exercise type detector 10. Steps 23 to 25 take about 1 second of calculation time. After this, the next measurement period is started in step 26. This alternation between a measurement period and a period of processing measurement results can continue for several days. For all this time, the information obtained of the user's exercise is saved in the device.

The classification method utilized in the classification method according to the invention will be described in more detail in the following. The primary task of the exercise type detector 10 is to detect, analyse and save parameters defined from the signals coming from the acceleration transducers in three dimensions. In practice, accelerations of the three dimensions are preferably measured in periods of four seconds in both the positive and negative direction. During the fifth second, a few central measurement data, such as maximum and minimum values and averages are separated from these measurement signals. These values are compared to comparison values, by means of which the measurement results are classified preferably into at least eight subgroups, which have been presented in Table 1.

TABLE 1

Subgroup division of the comparison table

| Number | Abbreviation |
|---|---|
| 0 | Unclassified or no result |
| 1 | SW; slow walking |
| 2 | NW; normal walking |
| 3 | SR; slow running |
| 4 | FR; fast running |
| 5 | SU; stairs up |

TABLE 1-continued

Subgroup division of the comparison table

| Number | Abbreviation |
|---|---|
| 6 | SD; stairs down |
| 7 | Self-selectable class |

There is preferably a plurality of subgroups in the comparison table. For example, there can be a number of subgroups describing slow walking. These subgroups of subgroups can be used, for example, to distinguish between the measurement results describing slow walking of people of different ages.

A change of height from the sea level always means a change in the atmospheric pressure. It is generally known that the change of height can be concluded by measuring the atmospheric pressure by an altimeter, for example. The classification of the comparison table can be advantageously made more accurate by taking a possible change of height into consideration. In the example of table 1, types of exercise in which a clear change of height takes place, are stairs up and down.

The classified results are saved in the memory of the exercise type detector 10, from which the information can be advantageously taken out either through a serial bus or a wireless link to a separate data processing device. The exercise type detector 10 normally repeats the sequence of 4+1 seconds without an interruption.

The signal analysis used in the exercise type detector 10 is preferably of the following kind. The transducers detect accelerations in the directions of the x, y and z dimensions/axes in both the positive and the negative direction in the range 0-10 g. The coordinates of the acceleration transducers preferably correspond to the following description:

the device is used on the right side of the user the left-right horizontal axis is the y coordinate, the plus axis on the right the backward-forward horizontal axis is the x coordinate, the plus axis forward the downward-upward vertical axis is the z coordinate, the plus axis upward Naturally, the device according to the invention can also be used on the left side of a person, in which case the directions of the coordinate axes are changed correspondingly in the program.

In the analysis, the component caused by the earth's gravity is removed by calculation. In other words, when the device is in a stable state in its place, the measurement value is 0 g.

The signals coming from the acceleration transducers are preferably sampled at the measurement frequency 100-400 Hz. Threshold levels are separately set for each dimension in the x, y and z directions, and these must be changeable through the serial bus in the range 0.1-1.5 g by steps of 0.1 g. By default, the threshold level is 0.3 g in each dimension to be measured. A hysteresis value in the order of +/−0.1 g is preferably set for the threshold level. On the same coordinate axis, both the positive and the negative threshold level must have the same absolute value. Signal levels that remain under the threshold level are not taken into account. When the coordinates are twisted in respect to the earth's gravity, static acceleration occurs on the x and y axes, which in turn may cause baseless exceedings of the threshold level. This phenomenon can be advantageously eliminated by increasing the threshold level of the x and y axes.

Exceeding of the threshold level taking place on any dimension/direction/axis causes a signal analysis operation on all three dimensions. The signals are monitored for four seconds, at the same time distinguishing the parameters mentioned below on each dimension, after which there is one second of time to analyze and classify the information gathered. The device preferably repeats the sequence of 4+1 seconds continuously, if the mode of operation is not changed.

The parameters used in the exercise type analysis method according to the invention will be presented in the following:

Max x, Max y, Max z

Min x, Min y, Min z

Sum x, Sum y, Sum z

Count x, Count y, Count z

Pos x count, Pos y count, Pos z count

Neg x count, Neg y count, Neg z count

The parameters Max x, Max y and Max z represent a positive peak value occurring during the measurement period in a certain dimension. Correspondingly, the parameters Min x, Min y and Min z represent a negative peak value observed during the measurement period in a certain dimension.

The parameters Sum x, Sum y and Sum z are used to calculate the cumulative sum of all measurement samples (accelerations) on the dimension in question, when the measurement operation has been started after exceeding either the positive or negative threshold level. The parameter Count x, Count y and Count z is related to the former, counting the number of samples occurring during the exceedings of both the positive and the negative threshold levels.

The parameters Pos x count, Pos y count and Pos z count present the number of pulses exceeding the positive threshold level. Correspondingly, the parameters Neg x count, Neg y count and Neg z count present the number of pulses exceeding the negative threshold level.

When the acceleration exceeds the maximum value of the scale (over 10 g), the maximum value 10 g is used in the analysis.

After the measurement period, the averages Avg x, Avg y and Avg z are calculated from the parameters Sum x, y, z and Count x, y, z. The results thus obtained are used in the classification of the measurement information, by means of which the type of exercise practised is found out. The subgroup division/classification according to Table 2 can be preferably utilized in the classification of the measurement results. In the example of Table 2, there are 6 different predetermined exercise classes in use, each of which contains 5 different exercise profiles, numbers 1 to 30. At the place of the profiles 4 and 5, the user can save their own profile from the exercise class in question. In addition, the user can save two freely selectable personal exercise profiles, numbers 31 to 32. The description of each exercise profile corresponds to the definitions presented in Table 1. The letter "O" at the beginning of a class definition indicates that the class is a class based on personal data. In the appropriate classification, each element of Table 2 has been given a numerical value describing it.

TABLE 2

Acceleration information classification table

| No. | Class | Max x | Max y | Max z | Min x | Min y | Min z | Avg x | Avg y | Avg z | Pos x count | Pos y count | Pos z count | Neg x count | Neg y count | Neg z Count |
|---|---|---|---|---|---|---|---|---|---|---|---|---|---|---|---|---|
| 1 | HK1 | | | | | | | | | | | | | | | |
| 2 | HK2 | | | | | | | | | | | | | | | |
| 3 | HK3 | | | | | | | | | | | | | | | |
| 4 | OHK1 | | | | | | | | | | | | | | | |
| 5 | OHK2 | | | | | | | | | | | | | | | |
| 6 | NK1 | | | | | | | | | | | | | | | |
| 7 | NK2 | | | | | | | | | | | | | | | |
| 8 | NK3 | | | | | | | | | | | | | | | |
| 9 | ONK1 | | | | | | | | | | | | | | | |
| 10 | ONK2 | | | | | | | | | | | | | | | |
| 11 | HJ1 | | | | | | | | | | | | | | | |
| 12 | HJ2 | | | | | | | | | | | | | | | |
| 13 | HJ3 | | | | | | | | | | | | | | | |
| 14 | OHJ1 | | | | | | | | | | | | | | | |
| 15 | OHJ2 | | | | | | | | | | | | | | | |
| 16 | NJ1 | | | | | | | | | | | | | | | |
| 17 | NJ2 | | | | | | | | | | | | | | | |
| 18 | NJ3 | | | | | | | | | | | | | | | |
| 19 | ONJ1 | | | | | | | | | | | | | | | |
| 20 | ONJ2 | | | | | | | | | | | | | | | |
| 21 | PY1 | | | | | | | | | | | | | | | |
| 22 | PY2 | | | | | | | | | | | | | | | |
| 23 | PY3 | | | | | | | | | | | | | | | |
| 24 | OPY1 | | | | | | | | | | | | | | | |
| 25 | OPY2 | | | | | | | | | | | | | | | |
| 26 | PA1 | | | | | | | | | | | | | | | |
| 27 | PA2 | | | | | | | | | | | | | | | |
| 28 | PA3 | | | | | | | | | | | | | | | |
| 29 | OPA1 | | | | | | | | | | | | | | | |
| 30 | OPA2 | | | | | | | | | | | | | | | |
| 31 | OVL1 | | | | | | | | | | | | | | | |
| 32 | OVL2 | | | | | | | | | | | | | | | |

In the following, the use of Table 2 in connection with determining the type of exercise will be described by means of a simplified 2-dimensional example (dimensions x and y). The example includes three walking profiles and three running profiles, the Max and Min values of which have been set according to Table 3. The same main exercise class, such as HJ, thus preferably includes many different tabulated values, HJ1-HJ3. By means of these variations, different persons' ways of moving that differ from each other slightly can be classified into the right exercise class.

TABLE 3

Examples of the values of classes

| No. | Class | Max x | Max y | Min x | Min y |
|---|---|---|---|---|---|
| 11 | HJ1 | 1.4 | 0.8 | −0.2 | −0.3 |
| 12 | HJ2 | 1.6 | 0.6 | −0.1 | 0.1 |
| 13 | HJ3 | 1.2 | 0.7 | 0.2 | −0.2 |
| 1 | HK1 | 0.8 | 0.4 | −0.1 | −0.2 |
| 2 | HK2 | 0.9 | 0.5 | −0.1 | 0.3 |
| 3 | HK3 | 1.0 | 0.6 | 0.1 | −0.1 |

In the example, the following series of measurement results is obtained from the acceleration transducers of the exercise type detector 10:

| Max x | Max y | Min x | Min y |
|---|---|---|---|
| 1.2 | 0.75 | −0.25 | −0.1 |

In the next step, this measurement result is compared to the values of the example table 3 by means of a so-called membership degree function. Each profile of the example table 3 has its own membership degree function, which preferably has a triangular shape. The centre of this triangular function is the numerical value presented in Table 3.

Figure 3:
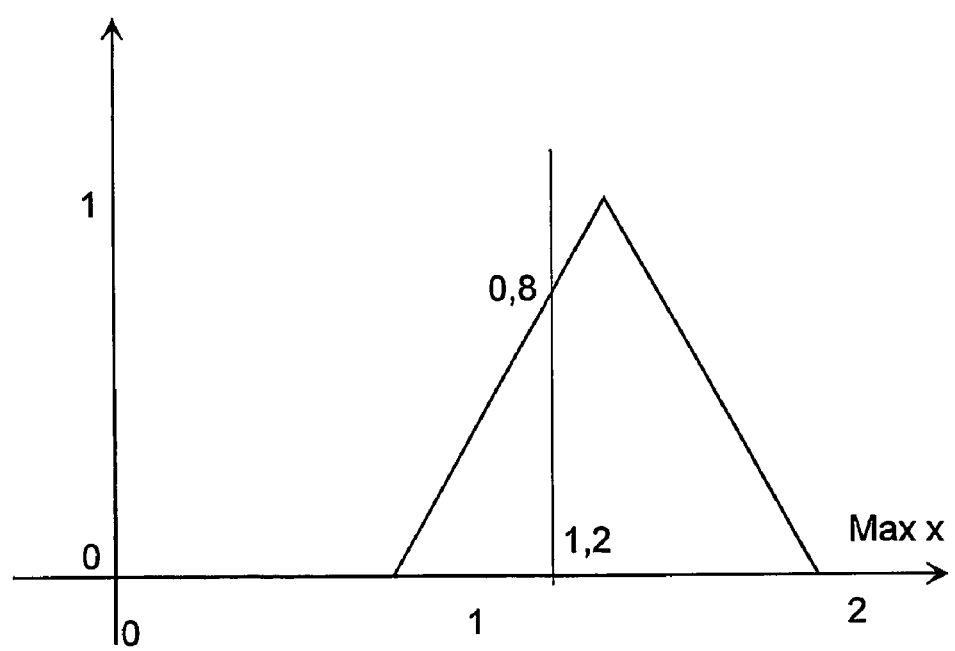
FIG. 3 shows an example of the membership degree function utilized in the invention.

The processing of the first measurement value Max x with respect to the profile HJ1 will be described in the following. According to the measurement, the Max x value is 1.2. The membership degree function of the profile HJ1 has been presented in FIG. 3. The height of the triangle presented in FIG. 3 is always 1. For this membership degree function, the width of the base of the triangle is 0.44 (the determination of the width will be described hereinafter).

The width w of the base of the membership degree function, the triangle in FIG. 3, is obtained in the following manner. At first, the difference between the largest value of each parameter and the smallest value of the same parameter is calculated. In the case of the example (HJ1)1.4−(HK1) 0.8=0.8 (range$_i$). The width of the triangle is then w=constant 1×range$_i$+abs(constant 2×value of the class).

The constants 1 and 2 can vary in the range 0.2-0.4. If, for example, 0.2 is taken as the value of the constants, it is possible to calculate for all the 3 Max x values of the table the width of the triangle of the membership degree function of each value in the table:

1.4=>0.2×0.8+abs(0.2×1.4)=0.44

1.6=>0.2×0.8+abs(0.2×1.6)=0.28

1.2=>0.2×0.8+abs(0.2×1.2)=0.40

0.8=>0.2×0.8+abs(0.2×0.8)=0.32

0.9=>0.2×0.8+abs(0.2×0.9)=0.34

1.0=>0.2×0.8+abs(0.2×1.0)=0.36

The calculated length of the base of the triangle is used for drawing the triangle presented in FIG. 3. The height of the triangle of the membership degree function is always 1. The centre of the triangle is the numerical value (HJ1=>1.4) shown by Table 3. In this exemplary case, the Max x value 1.2 of HJ1 originally measured from FIG. 3 gets the numerical value 0.8 of the membership function.

In a corresponding manner, membership degree functions are calculated for all the parameters of Table 3, and thereby a certain numerical value is obtained, as was described above in the case of Max x of HJ1. This calculation for all parameters gives the following result shown in table 4 in this exemplary case:

TABLE 4

The values of the membership function in the exemplary case of Table 2

| No. | Class | Max x | Max y | Min x | Min y | Aver | Min | Weighted |
|---|---|---|---|---|---|---|---|---|
| 11 | HJ1 | 0.8 | 0.6 | 0.6 | 0.5 | 0.6 | 0.5 | 0.55 |
| 12 | HJ2 | 0.6 | 0.6 | 0.71 | 0.6 | 0.65 | 0.6 | 0.625 |
| 13 | HJ3 | 0.5 | 0.7 | 0.7 | 0.4 | 0.6 | 0.4 | 0.5 |
| 1 | HK1 | 0.4 | 0.2 | 0.2 | 0.3 | 0.3 | 0.2 | 0.25 |
| 2 | HK2 | 0.2 | 0.3 | 0.3 | 0.6 | 0.35 | 0.2 | 0.275 |
| 3 | HK3 | 0.1 | 0.1 | 0.5 | 0.6 | 0.3 | 0.1 | 0.2 |

The class "Weighted" is obtained by the formula a×Aver+ b×Min, in which a+b=1. In this example, the value 0.8 has been used for a, and the value 0.2 for b.

Of the classes shown in the table, the one in which the exercise profile which had the largest weighted value is placed, is selected as the class describing the type of exercise. In this example, the largest weighted value is 0.625, which corresponds to the exercise profile HJ2. Thus the method according to the invention gives the result that the type of exercise being performed means slow running in this example.

When this exercise class estimation has been performed, the number of the exercise class (profile) in question is saved in the memory of the exercise type detector 10. Saving only this type number is advantageous, because it requires only a small amount of memory capacity. By using the estimation method according to the invention, it is possible to save information describing the exercise of several days in a device with a small memory.

Some preferred embodiments of the method and device according to the invention have been described above. The invention is not limited to the embodiments just described. For example, it is possible to utilize a membership degree function of some other form than the triangular function described. In addition, the inventive idea can be applied in numerous ways within the limits set by the claims.

What is claimed is:

1. A method for carrying out exercise type detection, in which method the accelerations caused by a person's physical exercise are measured by an exercise type detector (10) in at least one dimension at least two different characteristics describing the accelerations measured are calculated from the measurement results, characterized in that the detection of the type of exercise is carried out by comparing the characteristics calculated from the measurement results to the values of a table saved in the memory of the exercise type detector (10), describing the types of exercise, and by selecting the exercise type, the value of which in the table is closest to the characteristics calculated from the results of the measurement as the exercise type in question.

2. The method according to claim 1, characterized in that the accelerations are measured in three dimensions.

3. The method according to claim 2, characterized in that the following acceleration parameters/measurement results are used in the detection of the type of exercise, Max x, Max y, Max z, Min x, Min y and Min z.

4. The method according to claim 3, characterized in that in addition, the following characteristics calculated from the acceleration measurement results are used in the detection of the type of exercise: Avg x, Avg y, Avg z, Pos x, Pos y, Pos z, Neg x, Neg y and Neg z.

5. The method according to claim 4, characterized in that in the detection of the type of exercise, the membership degree function of all the above mentioned parameters is calculated specifically for each exercise type to be examined.

6. The method according to claim 5, characterized in that a triangular function is used as the membership degree function.

7. The method according to claim 5, characterized in that in the detection of the type of exercise, the type of exercise, for which the weighted sum of the summed membership degree functions gives the highest numerical value, is detected.

8. The method according to claim 2, characterized in that in addition to the acceleration measurement, an altitude measurement is used in the exercise type detection to indicate vertical movement of the person.

9. The method according to claim 8, characterized in that the altitude measurement is based on a change of atmospheric pressure, which is measured either by a sensor in the exercise type detector (10) or other device carried along by the person, from which the altitude information is transferred to the exercise type detector.

10. The method according to claim 6, characterized in that in the detection of the type of exercise, the type of exercise, for which the weighted sum of the summed membership degree functions gives the highest numerical value, is detected.

11. An exercise type detector (10), which comprises
means (11) for measuring acceleration in at least one dimension
means for calculating (12) at least two different characteristics from the measured acceleration information, and
means (12) for saving the exercise type detection,
characterized in that the exercise type detector also comprises a table arranged by types of exercise, to the values of which the characteristics calculated from the acceleration measurement have been arranged to be compared in order to perform the detection of the type of exercise.

12. The exercise type detector (10) according to claim 11, characterized in that the means (11) for measuring acceleration comprise means for measuring acceleration in three dimensions perpendicular to each other.

13. The exercise type detector (10) according to claim 12, characterized in that the table used in the detection of the type of exercise comprises values specific to the type of exercise, concerning the following parameters describing accelerations: Max x, Max y, Max z, Min x, Min y, Min z, Avg x, Avg y, Avg z, Pos x, Pos y, Pos z, Neg x, Neg y and Neg z.

14. The exercise type detector (10) according to claim 13, characterized in that the detection of the type of exercise has been arranged to be performed by means of membership degree functions calculated for the parameters.

15. The exercise type detector (10) according to claim 14, characterized in that a triangular function has been arranged to be used as the membership degree function.

16. The exercise type detector (10) according to claim 15, characterized in that in the detection of the type of exercise, the one for which the weighted sum of the summed membership degree functions gives the highest numerical value has been arranged to be the type of exercise detected.

17. The exercise type detector (10) according to claim 14, characterized in that in the detection of the type of exercise, the one for which the weighted sum of the summed membership degree functions gives the highest numerical value has been arranged to be the type of exercise detected.

18. The exercise type detector (10) according to claim 11, characterized in that it also comprises an altimeter for indicating the movement of the person taking place in the vertical direction.

19. The exercise type detector (10) according to claim 18, characterized in that the altimeter is a meter based on a change of the atmospheric pressure.

20. The exercise type detector (10) according to claim 19, characterized in that the altimeter based on atmospheric pressure is located either in the exercise type detector (10) or a separate device carried along by the person, in which case the altitude information has been arranged to be transferred electrically to the exercise type detector (10).

21. A computer program product to be used in the exercise type detector (10) for performing the exercise type detection by using acceleration measurements, characterized in that the computer program product comprises
computer readable code means for calculating at least two different characteristics from the accelerations measured
computer readable code means for comparing the calculated characteristics to the values of the table saved in the exercise type detector (10), and
computer readable code means for selecting the type of exercise, the value of which in said table is closest to the characteristics calculated from the results of the measurement.

22. The computer program product according to claim 21, characterized in that it comprises computer readable code means for calculating the following acceleration parameters/measurement results: Max x, Max y, Max z, Min x, Min y, Min z, Avg x, Avg y, Avg z, Pos x, Pos y, Pos z, Neg x, Neg y and Neg z.

23. The computer readable code product according to claim 22, characterized in that it comprises computer program means for defining a membership degree function for said parameters by type of exercise.

24. The computer program product according to claim 23, characterized in that it comprises computer readable code means for calculating a membership function by using a triangular function.

25. The computer program product according to claim 23, characterized in that in it comprises computer readable code means for detecting a type of exercise as the type of exercise for which the sum of the weighted, summed membership degree functions gives the highest numerical value.

26. The computer program product according to claim 24, characterized in that in it comprises computer readable code means for detecting a type of exercise as the type of exercise for which the sum of the weighted, summed membership degree functions gives the highest numerical value.

27. The computer program product according to claim 21, characterized in that it also comprises computer readable code means for utilizing the result of the altitude measurement in addition to the acceleration measurements in the exercise type detection.

* * * * *